United States Patent
Wall

(10) Patent No.: US 9,057,089 B2
(45) Date of Patent: *Jun. 16, 2015

(54) METHODS FOR NATURAL PRODUCT OPTIMIZATION

(71) Applicant: The University of Wyoming, Laramie, WY (US)

(72) Inventor: Daniel Wall, Laramie, WY (US)

(73) Assignee: THE UNIVERSITY OF WYOMING, Laramie, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/273,112

(22) Filed: May 8, 2014

(65) Prior Publication Data

US 2014/0287450 A1    Sep. 25, 2014

Related U.S. Application Data

(63) Continuation of application No. 12/996,914, filed as application No. PCT/US2009/049562 on Jul. 2, 2009, now Pat. No. 8,759,020.

(60) Provisional application No. 61/077,659, filed on Jul. 2, 2008.

(51) Int. Cl.
| | | |
|---|---|---|
| C12Q 1/02 | (2006.01) | |
| C12N 1/38 | (2006.01) | |
| C12N 15/01 | (2006.01) | |
| C12P 1/04 | (2006.01) | |
| C12P 39/00 | (2006.01) | |

(52) U.S. Cl.
CPC .. *C12Q 1/02* (2013.01); *C12N 1/38* (2013.01); *C12N 15/01* (2013.01); *C12P 1/04* (2013.01); *C12P 39/00* (2013.01)

(58) Field of Classification Search
None
See application file for complete search history.

(56) References Cited

FOREIGN PATENT DOCUMENTS

WO      WO 9841869 A1      9/1998

OTHER PUBLICATIONS

Pham, V.D., et al. "Mutations affecting predation ability of the soil bacterium *Myxococcus xanthus*." Microbiology. Jun. 2005;151(Pt 6):1865-74.

Berleman, J.E., et al. "Multicellular development in *Myxococcus xanthus* is stimulated by predator-prey interactions." J Bacteriol. Aug. 2007;189(15):5675-82. Epub May 18, 2007.

Simunovic, V., et al. "Myxovirescin A biosynthesis is directed by hybrid polyketide synthases/nonribosomal peptide synthetase, 3-hydroxy-3-methylglutaryl-CoA synthases, and trans-acting acyltransferases." Chembiochem. Aug. 2006;7(8):1206-20. Abstract Only.

Berleman, J.E., et al. "Deciphering the hunting strategy of a bacterial wolfpack." FEMS Microbiol Rev. Sep. 2009;33(5):942-57. Epub May 9, 2009.

Gerth, K., et al. "Myxobacteria: proficient producers of novel natural products with various biological activities—past and future biotechnological aspects with the focus on the genus Sorangium." J Biotechnol. Dec. 19, 2003;106(2-3):233-53. Abstract Only.

Varon, M., et al. "Mutation and mapping of genes involved in production of the antibiotic TA in *Myxococcus xanthus*." Antimicrob Agents Chemother. Oct. 1992;36(10):2316-21.

Weissman, K.J., et al. "A brief tour of myxobacterial secondary metabolism." Bioorg Med Chem. Mar. 15, 2009;17(6):2121-36. Epub Nov. 18, 2008.

Simunovic, V. "Biosynthesis and Regulation of Production of the Antibiotic Myxovirescin A in *Myxococcus zanthus* DK 1622." Disseration zur Erlangung des Grades des Doktors der Naturwissenschaften—Technischen Fakultat III (Chemie, Pharmazie, Bio- und Werkoffwissenschaften) der Universitat des Saarlandes. May 2007.

Meiser. "*Myxococcus xanthus*—a myxobacterial model strain as multiproducer of secondary metabolites." Dissertation zue Erlangung des Grades des Doktors der Naturwissenschaften der Naturwissenschaftlich-Technischen Fakultat III (Chemie, Pharmazie, Bio- und Werkstoffwissenschaften) der Universitat des Saarlandes. 2008.

Rosenberg, et al., Autocides and a paracide, antibiotic TA, produced by *Myxococcus xanthus*, 1996, Journal of Industrial Microbiology 17(5-6):424-431.

*Primary Examiner* — Robert Yamasaki

(74) *Attorney, Agent, or Firm* — Robert C. Netter, Jr.; Kathleen D. Rigaut; Dann, Dorfman, Herrell & Skillman

(57) ABSTRACT

Methods and compositions for natural product optimization are provided. In particular, methods and compositions for selecting bacterial strains (e.g., predatory bacteria such as myxobacteria) which produce a desired compound (e.g., antibiotic, antifungal, or anticancer agent) are provided.

16 Claims, 8 Drawing Sheets

E

F

G

H

I

J

METHODS FOR NATURAL PRODUCT OPTIMIZATION

This application is a continuation application of U.S. patent application Ser. No. 12/996,914, filed on Jan. 17, 2011, which is a §371 application of PCT/US2009/049562, filed Jul. 2, 2009, which claims priority under 35 U.S.C. §119(e) to U.S. Provisional Patent Application No. 61/077,659, filed on Jul. 2, 2008. The entire disclosure of each of the foregoing applications is incorporated by reference herein.

FIELD OF THE INVENTION

The present invention relates to drug optimization. More specifically, the invention relates to methods of selecting bacterial strains, particularly myxobacteria strains and other predatory gliding bacteria, which produce a desired antibiotic, antifungal, or anticancer compound.

BACKGROUND OF THE INVENTION

Several publications and patent documents are cited throughout the specification in order to describe the state of the art to which this invention pertains. Each of these citations is incorporated by reference herein as though set forth in full.

The discovery and implementation of antibiotic drugs nearly 70 years ago revolutionized human medicine. Just a short time ago infectious diseases were the number one killer of Americans. Largely because of antibiotic development, infectious disease is no longer the leading cause of death in the U.S. and the average life expectancy has increased by nearly 30 years. The spectacular advancement of antibiotics from the mid-1940's to 1961 lead the U.S. Surgeon General to proclaim before Congress in 1969 that it is "time to close the book on infectious disease as a major health threat." In the decades that followed, it was found that heavy antibiotic use had resulted in an alarming increase in bacterial resistance (Talbot et al. (2006) Clin. Infect. Dis., 42:657-668). In parallel to the increase in resistance, major pharmaceutical companies abandoned antibiotic discovery in favor of life style and chronic disease drugs that offer larger profit margins. Consequently, only two novel classes of antibiotics have been introduced in the past 35 years. In 2004, the Infectious Disease Society of America released a report that a public health crisis is brewing as antibiotic research stagnates. Statics support this claim: (i) 70% of hospital acquired infection are resistant to at least one major class of antibiotics; (ii) 2 million patients acquire hospital bacterial infections per year resulting in >90,000 deaths, a number that has increase 6-fold since 1992, (iii) drug resistant infections cost the U.S. economy $5 billion annually, and (iv) a number of pathogens, such as methicillin resistance *Staphylococcus aureus* (MRSA) which represents 70% of *S. aureus* hospital acquired infections, are multidrug resistant and difficult to treat with existing antibiotics. Because of these factors there is an urgent need to discover and develop new antibiotics that work by novel mechanism (Talbot et al. (2006) Clin. Infect. Dis., 42:657-668; Norrby et al. (2005) Lancet Infect. Dis., 5:115-119; Payne, D. J. (2008) Science 321:1644-1645).

Natural products (NPs), which are by far the leading source of antibiotics, are developmentally hindered by low fermentation yields and structural complexity that make synthesis and optimization difficult (Walsh, C. (2003) Nat. Rev. Microbiol., 1:65-70; Baltz, R. (2007) Microbe 2:125-131; Demain et al. (2008) Prog. Drug Res., 65:251,253-289). For these and other reasons, pharmaceutical companies have largely abandoned NPs and developing new antibiotics (Walsh, C. (2003) Nat. Rev. Microbiol., 1:65-70; Baltz, R. (2007) Microbe 2:125-131; Baltz, R. H. (2008) Curr. Opin. Pharmacol., 8:557-563; Overbye et al. (2005) Drug Discov. Today 10:45-52; Nathan et al. (2005) Nat. Rev. Drug Discov., 4:887-891). Even with the advent of robotics and high-throughput technology, laborious screens used by pharmaceutical industries are still limited in their ability to process tens to hundreds of thousands of mutants (Demain et al. (2008) Prog. Drug Res., 65:251,253-289; Baltz, R. H. (2001) Antonie Van Leeuwenhoek, 79:251-259). To date, predation has not been utilized for natural product optimization, in part, because the major natural product producers (actinomycetes) are not predatory bacteria.

SUMMARY OF THE INVENTION

In accordance with one aspect of the instant invention, methods for screening for a natural product producing strain of a predatory microorganism are provided. In one embodiment, the method comprises: obtaining a predatory microorganism, culturing the predatory microorganism under conditions wherein they kill and consume prey cells, and isolating a predatory microorganism(s) which grows on the prey cells (e.g., the predatory organism which grows best). In one embodiment, the predatory microorganisms are cultured under conditions wherein prey cells are the only nutrient source. In a particular embodiment, the predatory microorganism cannot utilize (prey) on the prey cells (i.e., prior to the selective pressure of the culturing step).

In yet another embodiment, the method comprises: obtaining a predatory microorganism, mutagenizing the predatory microorganism (e.g., contacting the predatory microorganism with a chemical or physical mutagen or directed nucleic acid mutagenesis (e.g., ta1 knockout), culturing the mutagenized predatory microorganism under conditions wherein they kill and consume prey cells (e.g., wherein the only nutrient source is prey cells), and isolating a mutagenized predatory microorganism(s) which grows better on the prey cells than the unmutagenized predatory microorganism. In a particular embodiment, the unmutated or wild-type predatory microorganism cannot utilize (prey) on the prey cells.

The predatory microorganism of the instant methods may be a myxobacteria or other predatory gliding bacteria. Furthermore, the prey cell may be a bacteria, fungus, parasite, mammalian cell, or cancer cell. The methods may also further comprise isolating the natural product(s) produced by the isolated mutagenized predatory microorganism. In another embodiment, the natural product may be an antimicrobial compound, an antibiotic compound, an antifungal compound, an anticancer compound, or an antiparasitic compound. In another embodiment, the natural product is secreted by the predatory microorganism.

DETAILED DESCRIPTION OF THE INVENTION

Figure 1:
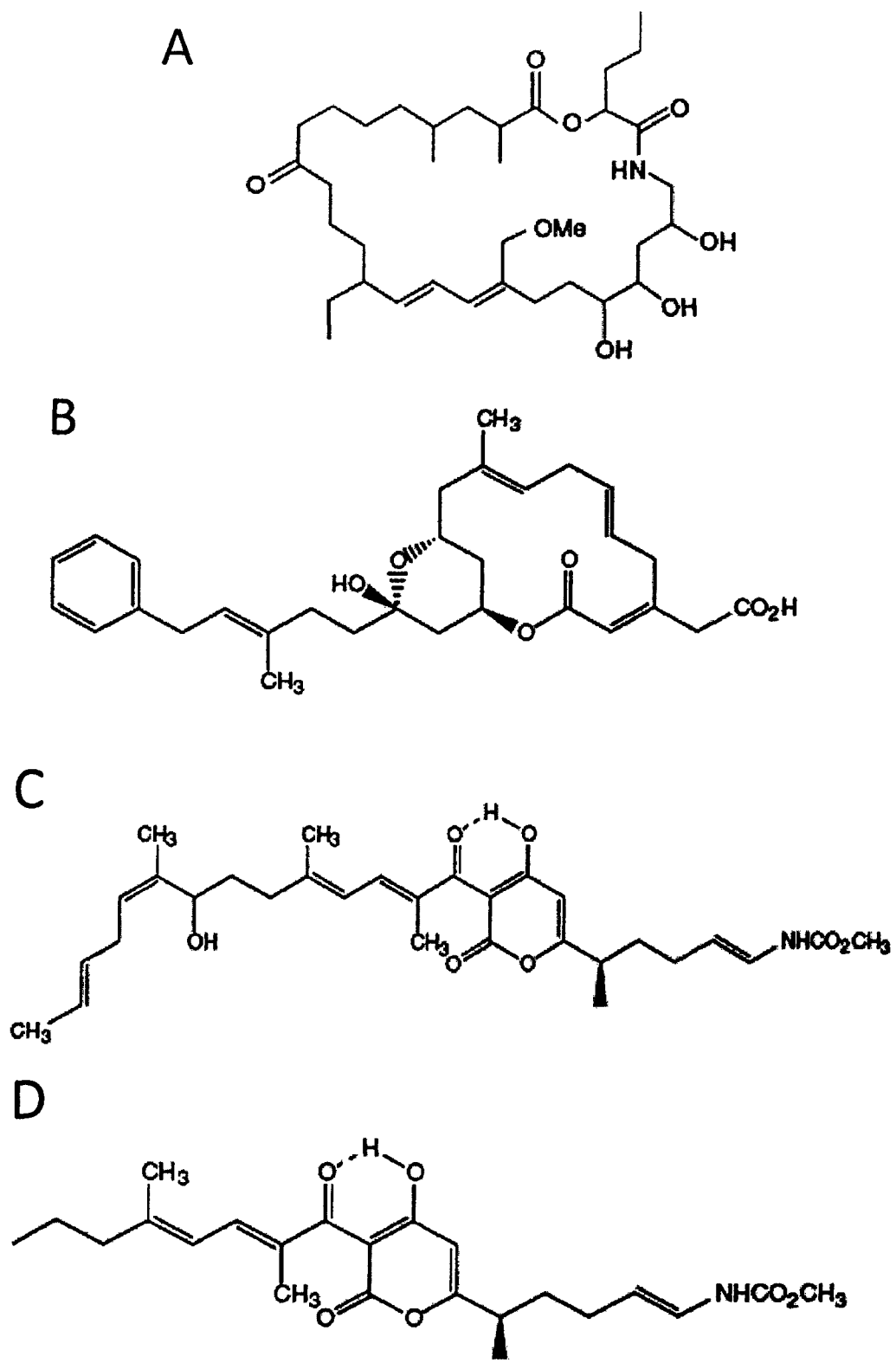
FIGS. 1A-1J provide the structures of secondary metabolites produced by gliding bacteria and have antibacterial activity. All compounds are produced by myxobacteria, except TAN-1057, which is produced by Flexibacter. The compounds are: A) antibiotic TA, B) ripostatin, C) corallopyronin, D) myxopyronin, E) sorangicin A, F) tartrolon, G) sorangiolid, H) angiolam, I) althiomycin, and J) TAN-1057.
Figure 1:
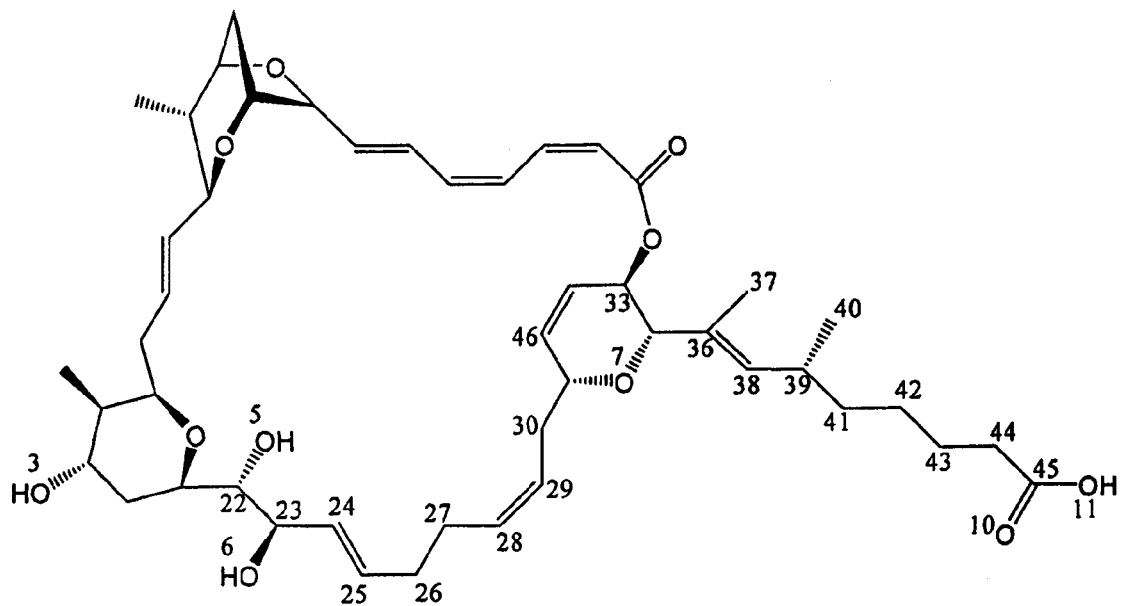
Figure 1:
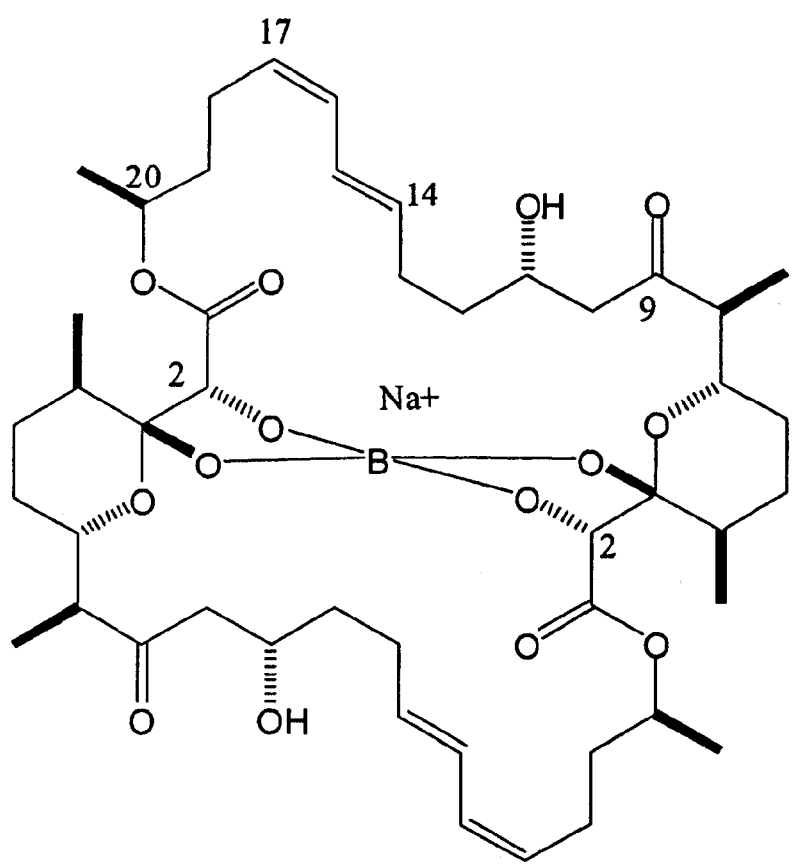
Figure 1:
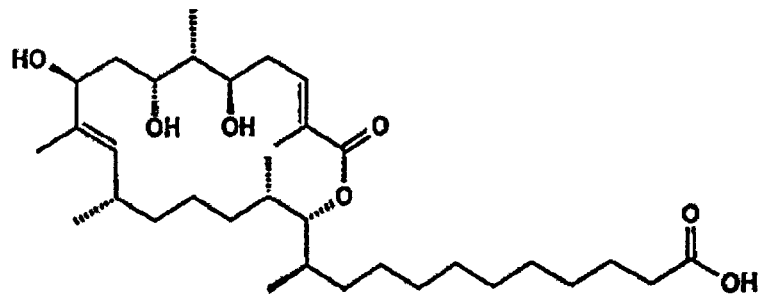
Figure 1:
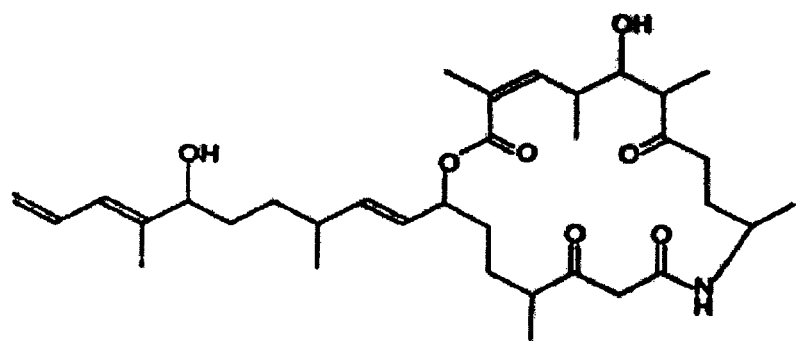
Figure 1:
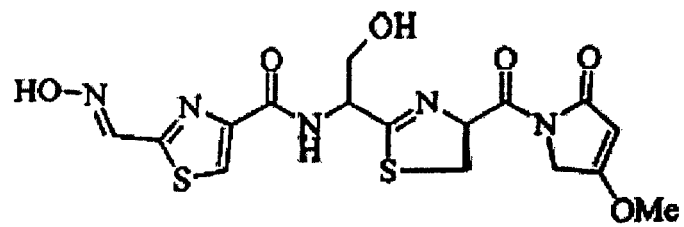
Figure 1:
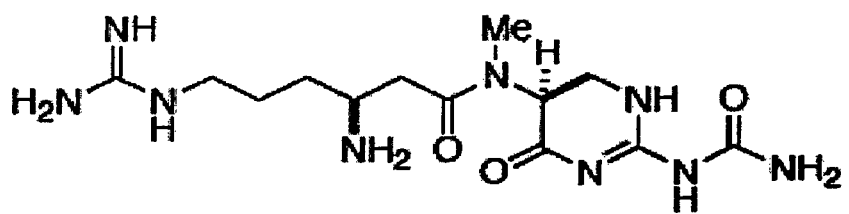

The instant invention provides methods for natural product optimization. More specifically, the instant invention provides new methods which exploit the predatory behavior of certain microorganisms, including myxobacteria and other predatory gliding bacteria (e.g., lysobacter, cyctophaga, flexibacter, and pseudomonads). Optimized strains for natural product (e.g., antibiotic) production are subsequently selected in accordance with the methods provided herein.

The instant invention provides a new means to optimize antibiotic production in predatory microorganisms such as myxobacteria. The vast majority of antibiotics to date are derived from natural products (e.g., aminoglycosides, macrolides, ketolides, tetracyclines, vanomycin, β-lactams (e.g., penicilliums, cephalosporins, monobactams), rifampin, fosfomycin, bacitracin, streptogramins, and daptomycin). The major synthetic exceptions are fluoroquinolones, sulfonamides, and oxazolidones. Natural products provide a rich source of chemical diversity and complexity (Clardy et al. (2006) Nat. Biotechnol., 24:1541-1550). Furthermore, natural product antibiotics are particularly useful because they evolved over time to have broad antibacterial activity and generally act on more than one molecular target, which generally makes resistance development difficult. In contrast, these properties are difficult to design into synthetic compounds. Further, natural products are complex structures that make chemical synthesis difficult. In addition, the major secondary metabolite producers, such as the Actinomycetes (which are not predatory organisms), have already been heavily mined by the pharmaceutical industry resulting in very few new structures being found. The instant invention overcomes the above shortcomings with previous natural product antibiotics.

Although myxobacteria are a prolific source of secondary metabolites (Reichenbach, H. (2001) J. Ind. Microbiol. Biotechnol., 27:149-156), including over 20 basic antibiotic (antibacterial and antifungal) structures, they have largely been overlooked for new therapeutics. To date, 100 basic structures and 500 structural variants have been characterized (Bode et al. (2006) J. Ind. Microbiol. Biotechnol., 33:577-588). These NPs have been found with relatively small screening efforts (Reichenbach, H. (2001) J. Ind. Microbiol. Biotechnol., 27:149-156; Reichenbach et al. (1993) Biotechnol. Adv., 11:219-277). Most of these natural products represent novel structures and elicit interesting biological responses. For instance, about 20 of the basic structures are antibiotics and many of these compounds represent excellent leads for optimization. For example, aside from TA, myxopyronin/corallopyronin offer promise as bacterial RNA polymerase inhibitors (Mukhopadhyay et al. (2008) Cell 135:295-307). Another promising myxobacterial NP are the epothilones, which inhibit microtubule depolymerization similar to paclitaxel (Donovan et al. (2008) Oncology 22:408-416).

Preliminary data is provided herein which shows that predatory microorganisms, such as myxobacteria, produce antibiotics to kill and eat prey organisms. The methods of the instant invention describes how genetic selection can be used to isolate strains that overproduce natural productions, produce different ratios of existing analog natural products, make new analog natural products, and/or turn on cryptic biosynthetic pathways (i.e., not normally expressed) to produce new antibiotics. These methods are superior to the laborious screens for strain optimization historically used in industry. Indeed, enormous numbers, e.g. about $10^{10}$ to $10^{12}$ or greater, of cells can be processed for rare mutants that exhibit improved activity by the instant methods. Traditional industrial screening procedures can only process about $10^3$ to $10^5$ mutants for optimal activity.

Myxobacteria are prolific producers of secondary metabolites in which ~500 novel basic and derivative structures have been found. A few examples of such compounds are provided in FIG. 1. Many of the secondary metabolites and derivatives produced by myxobacteria have antimicrobial activity. Myxobacteria are only exceeded by the actinomycetes and the genus *Bacillus* in the number of known structures produced. Unlike these bacteria, myxobacteria are predatory. They glide or swarm over solid surfaces and feed as microbial "wolf packs." Prey bacteria are digested by the secretion of a battery of hydrolytic enzymes including proteases, lipases, nucleases, and cell wall degrading enzymes. While the role of antibiotic production on predatory behavior had not previously been definitively established, data is provided herein which shows that antibiotic production serves to neutralize or kill prey microbes which then allows the hydrolytic enzymes to digest prey cells. Indeed, the hydrolytic enzymes may not be active on live cells because they may not be able to penetrate live cells, particularly the outer membrane of Gram-negative bacteria. Moreover, live cells can repair damage caused by hydrolytic enzymes. In contrast, small molecule antibiotics can penetrate cellular membranes and block cellular metabolism and compromise membrane integrity, thereby allowing the hydrolytic enzymes to degrade the cell. Based on the above, antibiotic production is essential under conditions where myxobacteria must kill and digest prey cells to survive. By extension, conditions can be devised for the selection and isolation of mutant myxobacteria with improved antibiotic production.

In accordance with one aspect of the instant invention, methods for drug optimization are provided. In a particular embodiment, the methods comprise maintaining a predatory microorganism under culture conditions wherein the only nutrient source is prey cells (e.g., bacterial cells) which cannot be utilized by the predatory microorganism. The predatory microorganism may be defective in predation (e.g., because the prey is naturally resistant or prey is engineered or mutagenized to be resistant) and cannot grow or swarm when the prey cells are the sole nutrient source. Similarly, under semi-rich growth conditions defects in microbial predation may allow prey cells to grow and consequently inhibit predatory growth by depletion of competing nutrients and/or physically blocking predator cells from swarming. The methods may further comprise mutagenizing (introducing a mutation into the cell) the predatory microorganism and selecting those cells which demonstrate increased predation of the prey cells (e.g., when presented as the only nutrient source). The methods may optionally further comprise identifying the natural products produced by the selected cells. In a particular embodiment, the methods of the instant invention may comprise multiple rounds of selection (e.g., multiple rounds of culturing with prey cells, optionally, with repeated mutagenization).

The predatory microorganism may be mutagenized by any means known in the art. Means for producing mutants are known to those skilled in the art and include, without limitation, the use of chemical and physical mutagens as well as targeted nucleic acid mutagenesis (e.g., insertional mutagenesis by introducing nucleic acid molecules (e.g., genes) into the cells). The mutants may also be spontaneous. Chemical mutagens include, without limitation, EMS (ethyl methane sulfonate; methanesulfonic acid ethyl ester), N-ethyl-N-nitrosourea (ENU), N-methyl-N-nitrosourea (MNU), procarbazine hydrochloride, chlorambucil, ICR191, cyclophosphamide, methyl methanesulfonate (MMS), diethyl sulfate, acrylamide monomer, triethylene melamine (TEM), melphalan, nitrogen mustard, vincristine, bromodeoxyuridine, dimethylnitrosamine, N-methyl-N'-nitro-Nitrosoguani-dine (MNNG), 7,12 dimethylbenzanthracene (DMBA), ethylene oxide, hexamethylphosphoramide, bisulfan, methane sulfonate, dimethyl sulfonate, O-6-methyl benzadine, ethidium bromide, tamoxifen, 8-hydroxyguanine, and derivatives and analogs thereof. In a particular embodiment, the chemical mutagen is selected from the group consisting of EMS, ICR191, and MNNG. Physical mutagens include, without limitation, the irradiation of cells (e.g., ultraviolet irradiation and ionizing irradiation (gamma, beta, and alpha irradiation and x-rays irradiation). In a particular embodiment, the physical mutagen is ultraviolet irradiation. With regard to the targeted nucleic acid mutagenesis, DNA can be inserted into the chromosome(s) of the microorganism or present on autonomously replicating plamsids. New genes (i.e., from other sources) can be provided or native genes can be duplicated or provided in multiple copies. Moreover, cloned DNA on a plasmid can be randomly or rationally mutagenized and transformed cells can be selected for improved antibiotic activity. For example, an antibiotic biosynthetic gene cluster (or individual genes) can be mutagenized by low fidelity PCR or chemical/UV mutagenesis creating a library of mutant clones, which can be subsequently transformed into predatory bacteria, selecting for improved predation.

Predatory microorganisms (e.g., predatory gliding bacteria) which can be used in the instant invention include, without limitation, myxobacteria (e.g., *Myxococcus xanthus*, *M. stipitatus*, *M. virescens* and *M. fulvus*; myxobacteria within suborder Cystobacterinea (e.g., *Archangium*, *Corallococcus*, *Cystobacter*, *Melittangium*, and *Stigmatella*); and myxobacteria within suborders Sorangineae and Nannocystineae (e.g., *Byssovorax*, *Chondromyces*, *Haliangium*, *Nannocystis*, *Polyangium*, and *Sorangium*)) and certain species within the genera *Lysobacter*, *Flexibacter*, *Pseudomonas* and *Burkholderia*, which are predators. The predatory microorganism may be also be genetically modified. For example, as described hereinbelow, foreign recombinant metabolite pathways may be introduced into the predatory microorganism for optimization by predator-prey selection. Additionally, the predatory microorganism may be modified to comprise a knockout of at least one gene essential for the production of a natural product produced by the predatory microorganism (e.g., a modification(s) and/or deletion(s) renders the naturally occurring gene nonfunctional). For example, as described hereinbelow, the ta1 gene may be knocked out of the predatory myxobacterium.

The cells selected for increased predatory action in the instant methods may, among other things, overproduce natural products, produce different ratios of natural products, and/or make new and novel derivatives of natural products. The methods of the instant invention may further comprise selecting for cells which have at least one of the above desired characteristics. For example, the cells selected for increased predation may be further screened to identify those which are overproducers of a desired natural product or antibiotic.

Further, the predation selective pressure can be used to select those cells which have an altered ratio of bioactive analogs. For example, some strains of myxobacteria are known make at least 30 closely related antibiotics called myxovirescins (also called antibiotic TA or megovalicins). The analogs have differential activity against different prey bacteria. Thus, when a particular prey is used for selection, the most potent derivative that is active on that particular prey can be selected for overexpression compared to other analogs/derivatives. In contrast, when a different prey is used under selection conditions the best/most potent derivative may be selected for overexpression with that prey compared to other analogs/derivatives.

Additionally, the mutagenesis and selective pressure on predation may be used to induce the synthesis of new natural products, which can be subsequently screened for. Indeed, the mutagenesis/selective pressure on predation can be used to induce expression of cryptic antibiotic pathways. For example, the *M. xanthus* (strain DK1622) genome has been sequenced and found to encode at least 18 gene clusters for natural products synthesis (Bode et al. (2006) J. Ind. Microbiol. Biotechnol., 33:577-588; Goldman et al. (2006) Proc. Natl. Acad. Sci., 103:15200-15205). However, only 5 secondary metabolites have been shown to be produced by this strain (Krug et al. (2008) Appl. Environ. Microbiol., 74:3058-3068). Thus, the other pathways are likely either not expressed or expressed at low levels during standard laboratory cultivation conditions. The selection process may result in the isolation of mutants that express those pathways, thereby facilitating predation.

In addition to increasing production or potency optimization, other properties of the natural product compound can be optimized. Such properties include, for example, the ability of a compound to penetrate target cells or not to be effluxed from target cells. Here, prey cells can be selected which have reduced permeability, such as *Pseudomonas* species or, alternatively, particular prey mutants with reduced permeability, such as *E. coli* mucoid mutants. If efflux is a parameter for optimization, then prey strains that over produce efflux pumps can be chosen as prey, or bacterial species that are known to have high levels of efflux pump activity can be chosen as prey. Physiochemical properties of the natural product, such as solubility, stability, or binding properties to surfaces or proteins, can also be optimized. To optimize each parameter selective conditions can be devised accordingly. For example, if improved solubility is sought, then predation conditions should be devised under liquid culture conditions. Predatory mutants that have improved predation ability under this condition may produce an antibiotic with improved solubility. If reduced serum albumin binding is sought, then protein albumin can be added to predation conditions as a binding competitor to select compound derivatives with reduced albumin binding.

The prey cells can be any microorganism or organism capable of being preyed on by the predatory microorganism. In a particular embodiment, the prey cells are cells that have obtained resistance to a natural product (e.g., antibiotic) produced by the predatory microorganism. For example, if a prey cell (e.g., an *E. coli* mutant) is resistant to the antibiotic myxopyronin (e.g., by generating a mutation in the target protein, RNA polymerase), then derivatives/analogs of myxopyronin may be synthesized by a mutagenized predatory microorganism which previously synthesized myxopyronin, such that the derivative/analog can now bind and inhibit that target. Notably, target and non-target prey cells can be constructed to optimize natural products with specific activities against the target cells but not the non-target cells.

In another embodiment, the prey microorganism is a fungal cell. As such, the natural product selected for may be an antifungal agent. For example, myxobacteria can prey on fungal organisms, including pathogenic organisms like *Candida albicans*, as a food source and are prolific producers of antifungal compounds. The instant methods can be used to, for example, identify overproducers, producers of novel antifungal compounds, and/or producers of different ratios of antifungal compounds/derivatives/analogs.

In still another embodiment, the prey organism is a multicellular organism such as, without limitation, parasitic worms such as nematodes. Certain predatory microorganisms are known to prey on and kill multicellular organism. Accordingly, the methods of the instant invention can be used to identify can be used to select and optimize anti-parasitic compound production.

In yet another embodiment, the prey cells may be eukaryotic or mammalian cells. Certain predatory microorganisms produce compounds that have known cytotoxic effect on mammalian cells. As a consequence these compounds have therapeutic potential for cancer treatment. For example, one compound produced by myxobacteria that has shown great promise in clinical trials to treat cancer is epothilone. This anti-cancer agent works by interfering with microtubule polymerization and consequently kills cancer cells. Accordingly, predatory microorganisms may be mutagenized and selected for their ability to predate on prey eukaryotic cells (e.g., mammalian or human cells or cancer cells) to allow for the selection of optimized production of natural products with eukaryotic cytotoxic effects, e.g., anti-cancer agents.

According to one aspect of the instant invention, the predation selection methods can also be employed for natural products that are heterologously produced in a predatory microorganism. The natural product may be expressed in a foreign predatory host. For example, the natural product epothilone has been expressed in a surrogate host by cloning the epothilone biosynthetic pathway from the endogenous producer, *Sorangium cellulosum*, into a heterologous *M. xanthus* host. The predation selection methods described herein can then be performed on the *M. xanthus* host comprising the epothilone biosynthetic pathway.

In accordance with another aspect of the invention, the compounds identified by the predation screening methods described herein may be used administered to a subject as a therapeutic (e.g., as an antibacterial, antifungal, anti-parasitic, anti-cancer agent). In a particular embodiment, the compound may be used an antibacterial agent against periodontal disease (e.g., oral administration). The isolated natural product may be contained within a composition comprising at least one pharmaceutically acceptable carrier.

According to another aspect of the instant invention, predators may be tested against prey cells in a fitness experiment. More specifically, predator cells and prey cells are mixed in culture or on plates and are allowed to compete for growth on rich or semi-rich media. Under rich media conditions, both cell types can grow because rich nutrients are used. Under semi-rich growth conditions, defects in microbial predation allow prey cells to grow and consequently inhibit predatory growth by depletion of competing nutrients and/or physically blocking predator cells from swarming. A predator that produces more/better antibiotic activity (e.g., more potent, improved solubility, improved stability, improved cell penetration, and/or reduced efflux) would kill and/or outcompete prey cells and other less competitive predator cells. This method can also be used with non-predatory antibiotic producers (e.g., actinomycetes). The fitness test may be used to further characterize the predatory microorganisms identified by the screening methods described herein (e.g., further select superior producers of antibiotic activity). In another embodiment, the fitness test may replace the step of screening for optimized natural product producers by using prey cells as the sole nutrient source, in the methods described above. For example, the mutagenized predatory cells can be subjected to a fitness test with prey cells and those mutagenized predatory cells which kill and/or outcompete prey cells better than other predatory cells can be enriched or isolated as optimized natural product producers. Multiple rounds may performed.

DEFINITIONS

The term "natural products" generally refers to compounds isolated from an organism and which are preferably identified as having a pharmacological activity.

The term "isolated" generally refers to material that is substantially or essentially free from components which accompanied the material prior to isolation. The term "isolated" is not meant to exclude artificial or synthetic mixtures with other compounds or materials, or the presence of impurities that do not interfere with the desired activity, and that may be present, for example, due to incomplete purification, or the addition of stabilizers.

A "carrier" refers to, for example, a diluent, adjuvant, excipient, auxilliary agent or vehicle with which an active agent of the present invention is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

"Pharmaceutically acceptable" indicates approval by a regulatory agency of the Federal government or a state government. "Pharmaceutically acceptable" agents may be listed in the U.S. Pharmacopeia or other generally recognized pharmacopeia for use in animals, and more particularly in humans.

Terms that refer to being "anti" a type of target organism or cell type (e.g., antimicrobial, antiviral, antifungal, antibacterial, antiparasite, anticancer) refers to having any deleterious effects upon those organisms or cells or their ability to cause symptoms in a host or patient. Examples include, but are not limited to, the inhibition or prevention of growth or reproduction, killing of the organism or cells, and/or the inhibition of any metabolic activity of the target organism. The term "antibiotic" refers to any substance or compound that when contacted with a living cell, organism, virus, or other entity capable of replication, results in a reduction of growth, viability, or pathogenicity of that entity. The term "anticancer agent" refers to compounds capable of inhibiting the proliferation of cancer cells (tumor cells) or killing cancer cells.

As used herein, the term "mutagen" refers to a compound or process that results in the introduction of mutations in the genome of an organism.

The following examples are provided to illustrate various embodiments of the present invention. They are not intended to limit the invention in any way.

EXAMPLE 1

Antibiotic TA is also known as myxovirescin, megovalicin and M-230B (Miyashiro et al. (1988) J. Antibiot., 41:433-438; Onishi et al. (1984) J. Antibiot., 37:13-19; Gerth et al. (1982) J. Antibiot., 35:1454-1459; Rosenberg et al. (1973) Antimicrob. Agents Chemother., 4:507-513). This broad-spectrum macrocyclic antibiotic is synthesized by a hybrid polyketide synthetase (PKS) and nonribosomal peptide synthetase (NRPS) (Simunovic et al. (2006) Chembiochem., 7:1206-1220). In DK1622, two variants have been described (Simunovic et al. (2006) Chembiochem., 7:1206-1220; compound 1 is shown as FIG. 1A; compound 2 replaces the =O at position 20 with H,H). Other myxobacteria species, such as *M. flavescens*, produce six variants, while *M. virescens* Mx v48 makes at least 30 variants (Simunovic et al. (2006) Chembiochem., 7:1206-1220; Gerth et al. (1982) J. Antibiot., 35:1454-1459). Some analogs have differential activity. For example, compound 2 has potent *Pseudomonas aeruginosa* activity (MIC ~1 μg/ml; Miyashiro et al. (1988) J. Antibiot., 41:433-438). The production of NP mixtures may serve a selective advantage, i.e. broader antibacterial spectrum.

Antibiotic TA is bactericidal and inhibits cell wall biosynthesis in Gram-negative and Gram-positive bacteria (Zafriri et al. (1981) Antimicrob. Agents Chemother., 19:349-351; Mukhopadhyay et al. (2008) Cell 135:295-307; Donovan et al. (2008) Oncology 22:408-416; Goldman et al. (2006) Proc. Natl. Acad. Sci., 103:15200-15205; Krug et al. (2008) Appl. Environ. Microbiol., 74:3058-3068). 99% of growing *E. coli* cells are killed within 30 minutes at 2 μg/ml of Antibiotic TA and activity is not inhibited by sera (Rosenberg et al. (1996) J. Indust. Microbiol., 17:424-431). Antibiotic TA is not active on fungi, protozoa, or eukaryotic cells and has been shown to be safe in animals and humans (Manor et al. (1989) J. Clin. Periodontol., 16:621-624; Rosenberg et al. (1996) J. Indust. Microb., 17:424-431). However, further development of TA has been hampered by difficult synthesis (~40 steps) and low fermentation yields (0.2 to 20 mg/L) (Content et al. (2003) Bioorg. Med. Chem. Lett., 13:321-325). Environmental isolates have been found to synthesize over 30 TA structural variants that exhibit differential antibacterial activity. Consequently, predation schemes might select for the production of particular variants, depending on the prey bacteria used.

Several lines of evidence indicate that TA inhibits bacterial cell wall biosynthesis, as stated hereinabove. In addition to bactericidal activity, TA treatment induces spheroplast production; a hallmark of cell wall inhibitors (Rosenberg et al. (1973) Antimicrob. Agents Chemother., 4:507-513). Metabolic labeling experiments show that TA blocks peptidoglycan synthesis (Zafriri et al. (1981) Antimicrob. Agents Chemother., 19:349-351; Gerth et al. (1982) J. Antibiot., 35:1454-1459) by inhibiting lipid II polymerization. TA does not inhibit the final cross-linking step catalyzed by transpeptidases (penicillin binding proteins, PBPs), the target of β-lactams (Zafriri et al. (1981) Antimicrob. Agents Chemother., 19:349-351). These data indicate that TA may block polymerization by inhibiting transglycosylase activity of PBPs, perhaps similar to moenomycin (Lovering et al. (2007) Science 315:1402-1405). Alternatively, TA may block translocation of lipid II from the cytoplasm to the periplasmic space (Silver, L. L. (2003) Curr. Opin. Microbiol., 6:431-438).

Antibiotic TA exhibits high adhesive properties toward biologic and non-biological material (Rosenberg, et al. (1984) Biotechnology, 796-799). For this reason, TA is a promising antibacterial agent to coat indwelling medical devices (such as catheters), and to prevent the formation of bacterial biofilms and the resulting, difficult-to-treat nosocomial infections (Simhi et al. (2000) FEMS Microbiol. Lett., 192:97-100). TA also strongly adheres to hard dental tissues with slow release times and extended antibacterial activity (Manor et al. (1985) J. Dent. Res., 64:1371-1373). These key characteristics, combined with good antibacterial activity against periodontal pathogens make TA a good antibiotic for dental applications. Indeed, human clinical trials showed that TA was an effective therapeutic for periodontal diseases (Manor et al. (1989) J. Clin. Periodontol., 16:621-624; Eli et al. (1988) Refuat. Hashinayim., 6:14-15). The results found that in only two treatments, three indices were significantly improved (plaque, gingival, and bleeding) and were long-lasting.

The ta1 gene encodes a polyketide synthase that is required for biosynthesis of the macrolide antibiotic TA (original isolate from Tel Aviv). The ta1 gene resides within an 83 kb gene cluster that encodes 21 gene products involved in TA biosynthesis. The ta1 gene and operon are not essential for growth in rich media (e.g., casitone).

A ta1 gene knockout construct may be made by PCR amplification of a 1.2 kb internal gene fragment, which may be TOPO cloned into the pCR2.1 plasmid. The resultant plasmid may be transformed into *E. coli* selecting kanamycin resistance. A validated clone may then be transformed into *M. xanthus* by again selecting Kan$^r$. This plasmid cannot replicate in *M. xanthus* and thus transformant are derived from homologous integration and gene disruption of the ta1 locus.

A defect in TA production may be determined in a bioassay, in which susceptible bacteria are streaked closely, but not touching, a mature *M. xanthus* colony. Alternatively, extracts may be purified from *M. xanthus* cultures and applied to a 5 mm diameter filter disk. This disk may be placed on a lawn of bacteria to measure the zone of inhibition of growth. Quantification of predation is scored by measuring swarm rates (plaques) on a lawn of susceptible prey as the only nutrient source. Notably, a single *M. xanthus* cell can give rise to a visible plaque (5-7 days). Different TA susceptible bacteria may be used as prey. Alternatively, *M. xanthus* strains are mixed with prey cells and at various times the rate of prey killing is measured by collecting and serially diluting prey cells and counting cfu on agar plates.

Figure 2A:
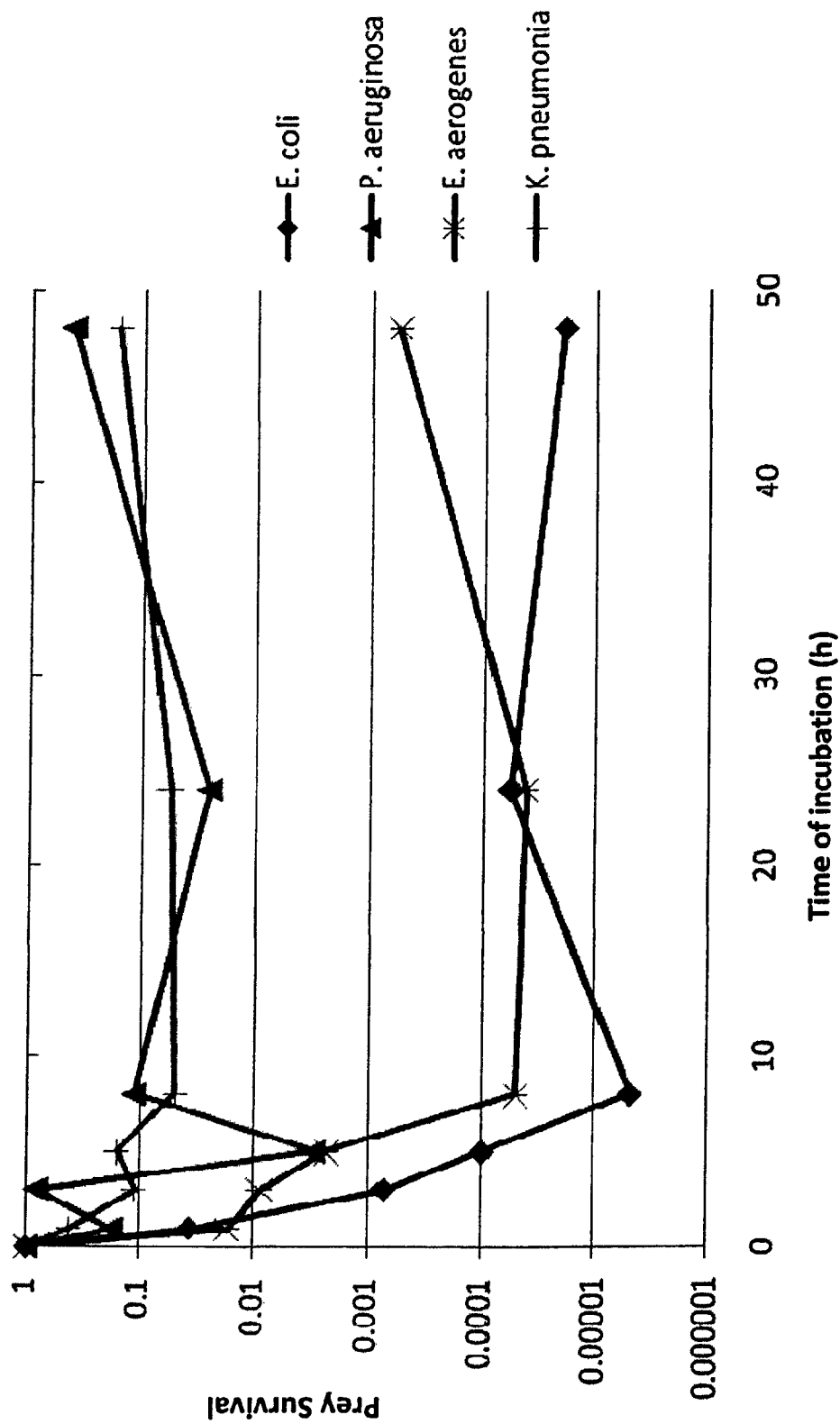
FIGS. 2A and 2B are graphs providing the fraction of survival of certain Gram-negative prey bacteria and Gram-positive prey bacteria, respectively, in the presence of *Myxococcus xanthus* (DK1622). Under these starvation conditions prey cells are fully viable (>three days). Bacteria were grown in rich media, concentrated, and then mixed in buffer (TPM) and spotted onto starvation agar plates. At various times, bacteria spots were collected and viable prey colony forming units (cfu) were measured on LB plates where *M. xanthus* growth is inhibited (high salt).
Figure 2:
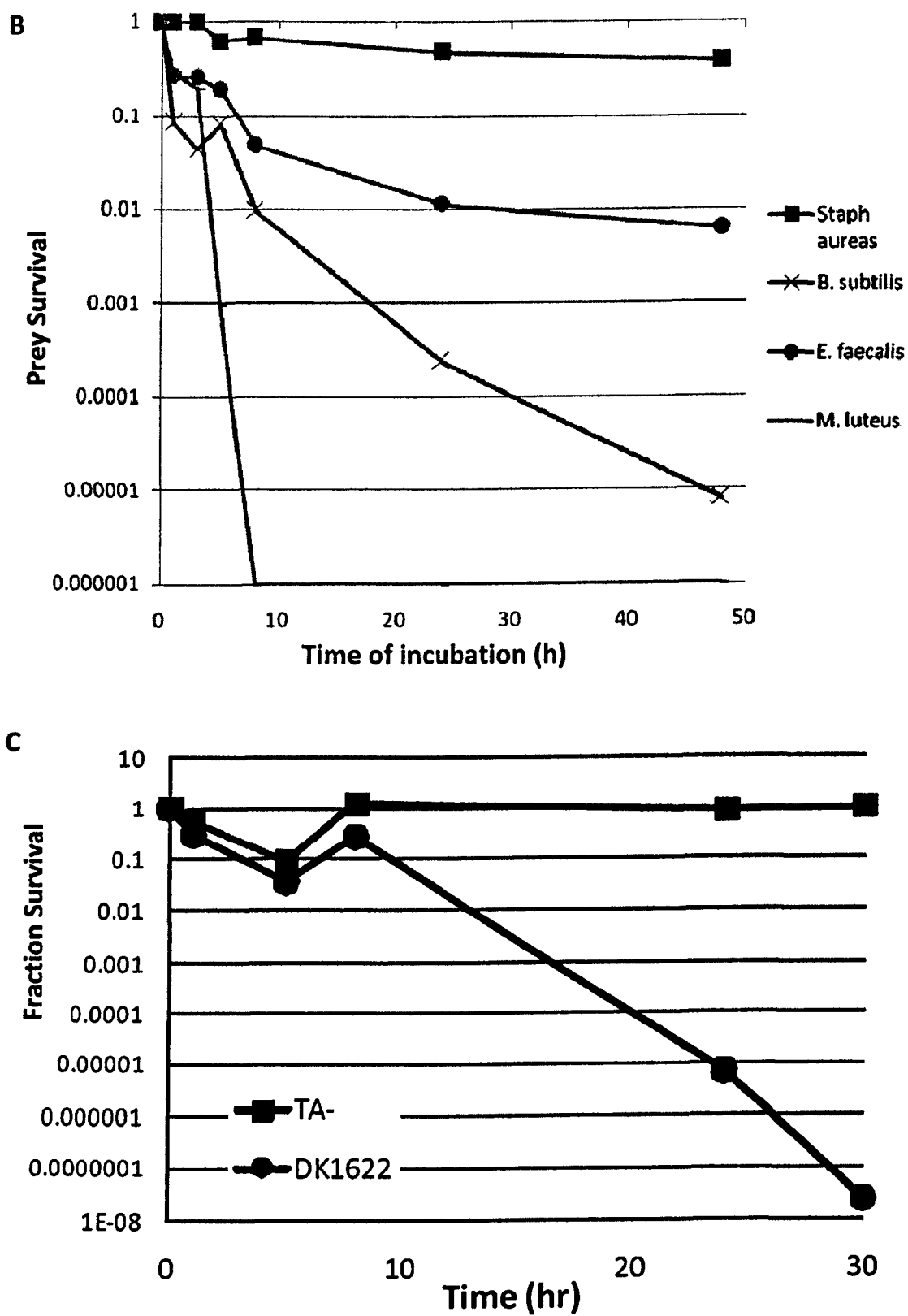
FIG. 2C is a graph demonstrating that antibiotic TA biosynthesis is required for predation. Isogenic strains of *Myxococcus xanthus* were compared for their predation activity on casitone-Tris (CTT) plates. TA-=DK1622 with an insertion mutation on the TA1 gene.

As seen in FIG. 2C, the ta1 mutant shows a dramatic defect in predation. To quantify the effect of the ta-mutation on prey killing, a predation assay was done on CTT agar plates (Wall et al. (1999) J. Bacteriol., 181:24-33). To help avoid the problem of non-specific killing of prey cells caused by *M. xanthus* autolysis during sample preparation, the *M. xanthus* cells were pre-spotted on a agar surface 2 hours prior to prey placement at a one-tenth ratio to prey cells (MG1655). FIG. 2C shows that the TA-mutant exhibits a drastic defect (>7-logs) in predation. The initial dip in prey killing is attributed to residual *M. xanthus* autolysing and release of hydrolytic enzymes that inevitably happens during *M. xanthus* sample preparation (Rosenberg et al. (1996) J. Indust. Microb., 17:424-431). These results clearly show that TA production plays a key role in predation.

Thus, the ta1 mutant exhibits a predation defect. Experimental conditions may be modified to accentuate a ta1 phenotype. Parameters which may be adjusted include prey, concentration of prey cells, buffer/salt, assay (liquid vs. agar plate), growth conditions of prey cells, and quantification methods (swarm rates vs. viable colony forming units). For example, *M. xanthus* does not utilize sugars as carbon/energy sources, thus simply adding glucose can selectively allow prey cell growth. It is also important to note that the physiology of prey cells, e.g. growth vs. stasis, can effect predation.

To assess the impact of TA antibiotic product on predation, an isogenic wild type and a ta1 mutant may be grown on a lawn of susceptible prey bacterial as the only source of nutrients. Quantification of predation ability is scored by measuring and plotting swarm rates (plaques) of the two *M. xanthus* strains. If the myxobacteria are able to kill and digest prey cells, the initial inoculum will grow and will spread or swarm in a concentric pattern through gliding motility over the agar surface. Bacteria that are known to be susceptible to antibiotic TA that will be used a prey cells include *Escherichia coli, Klebsiella pneumonia, Bacillus subtilis, Enterobacter aerogenes, Micrococcus luteus, Staphylococcus aureus,* and *Enterococcus faecalis* (see, e.g., FIGS. 2A and 2B).

EXAMPLE 2

To test predation as a selection means for antibiotic optimization, the ability of a ta1 mutant to revert back to the ta1$^+$ allele can be measured. In the absence of Kan$^R$ selection (plasmid retention) reversion occurs at a low frequency by homologous plasmid excision (reverse reaction of integration) resulting in a ta1$^+$ allele. To allow excision, the ta1 mutant may be grown for several days in rich casitone media in the absence of kanamycin. These cells may be harvested, washed, and applied to prey plates. Incubated plates may be visually inspected for swarming revertants. Putative revertants may be tested for Kan$^S$ (plasmid excision) and confirmed by PCR. Ta1 revertants will be able to grow and swarm on prey cells. Moreover, the selective condition may be sensitive to detect rare reversion events. The observance of revertants demonstrates the ability to use predation for antibiotic optimization. Notably, a certain threshold of revertant cells may be needed to be present to allow a pack of cells to kill, digest, and swarm over a prey lawn. To assess this parameter, wild type *M. xanthus* cells may be mixed at different ratios with ta1 mutants to determine assay sensitivity. Other experimental parameters such as buffers, salts, prey species, and conditions may need refined, as stated hereinabove.

EXAMPLE 3

Figure 3:
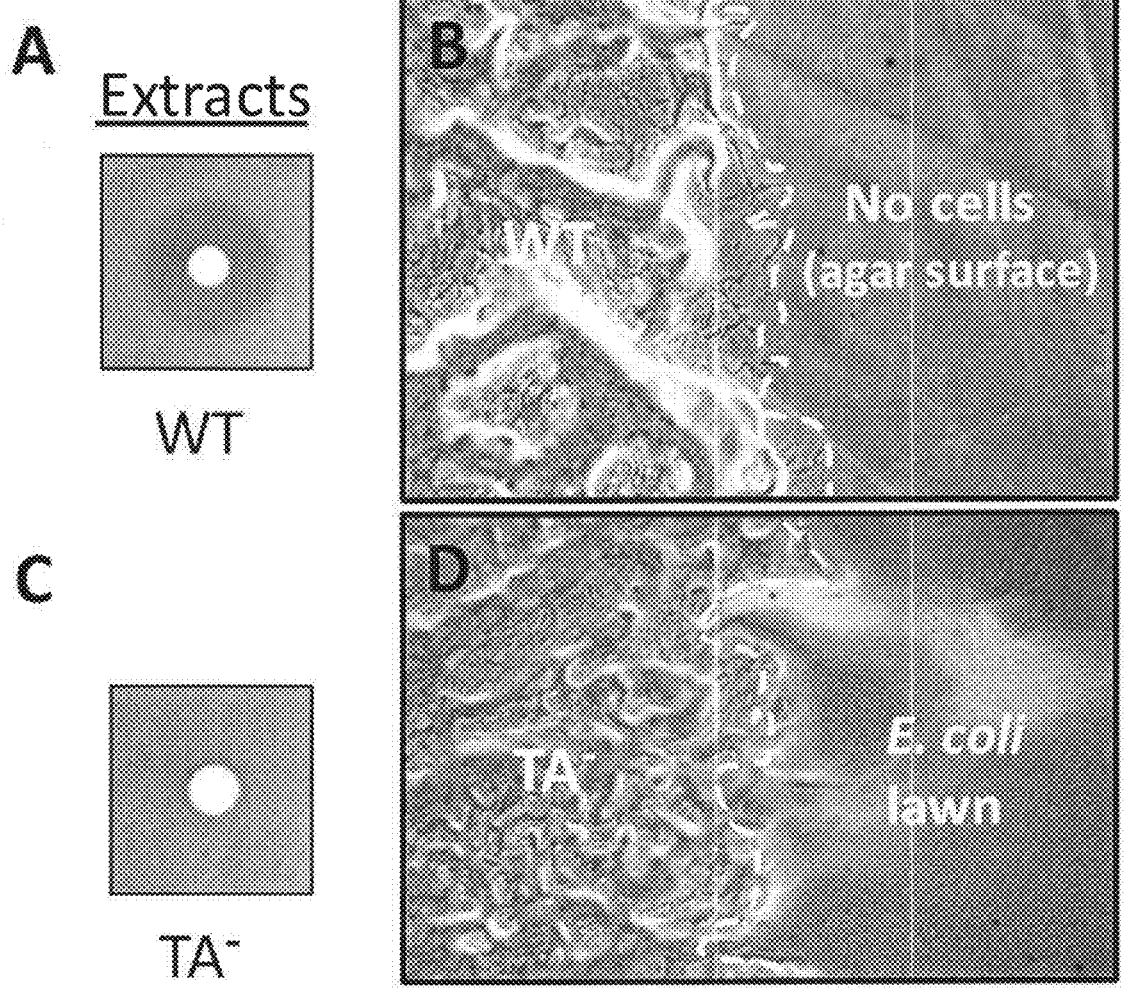
FIGS. 3A-3D demonstrate TA activity. DK1622 (WT) culture extract (FIG. 3A) and live swarm (FIG. 3B) inhibit *E. coli* indicator lawn growth. TA-extract (FIG. 3C) and live swarm (FIG. 3D) does not inhibit indicator lawn growth.

The biosynthetic pathway for antibiotic TA production is encoded within 21 ORFS that span an 83 kb region (Simunovic et al. (2006) Chembiochem., 7:1206-1220). To elucidate a possible role of TA in predation, the gene that encodes a major megasynthase, ta-1, was inactivated by homologous recombination with a suicide vector. The TA1 megasynthase (27 kb gene; 978 kDa protein) is essential for TA biosynthesis (Paitan et al. (1999) J. Mol. Biol., 286:465-474). The ta1 gene knockout was constructed by PCR amplification of a 1.2 kb internal gene fragment (size allows efficient recombination) and TOPO cloned into pCR2.1 (Invitrogen; Carlsbad, Calif.). A validated clone was then electroporated into *M. xanthus* and selected for homologous integration (Kan$^r$). A validated recombinant was then tested for antibiotic TA production with a bioassay. Here, an extract from the TA-mutant (ta1::kan) was prepared and activity compared to an extract prepared in parallel from WT cells. As shown, the crude extract prepared from the TA-mutant lacks antibiotic activity compared to WT (FIGS. 3A and 3C). Next, a live TA-mutant swarm was tested for antibacterial activity against an indicator lawn of *E. coli* cells. As shown in FIG. 3D, the TA-mutant swarm touches the *E. coli* lawn and does not form a zone of inhibition around the swarm edge. In contrast, the parental WT strain inhibits *E. coli* growth by forming a ~3 mm clear zone around the swarm edge (FIG. 3B). These results show that antibiotic TA plays an important role in killing bacteria.

EXAMPLE 4

Figure 4A:
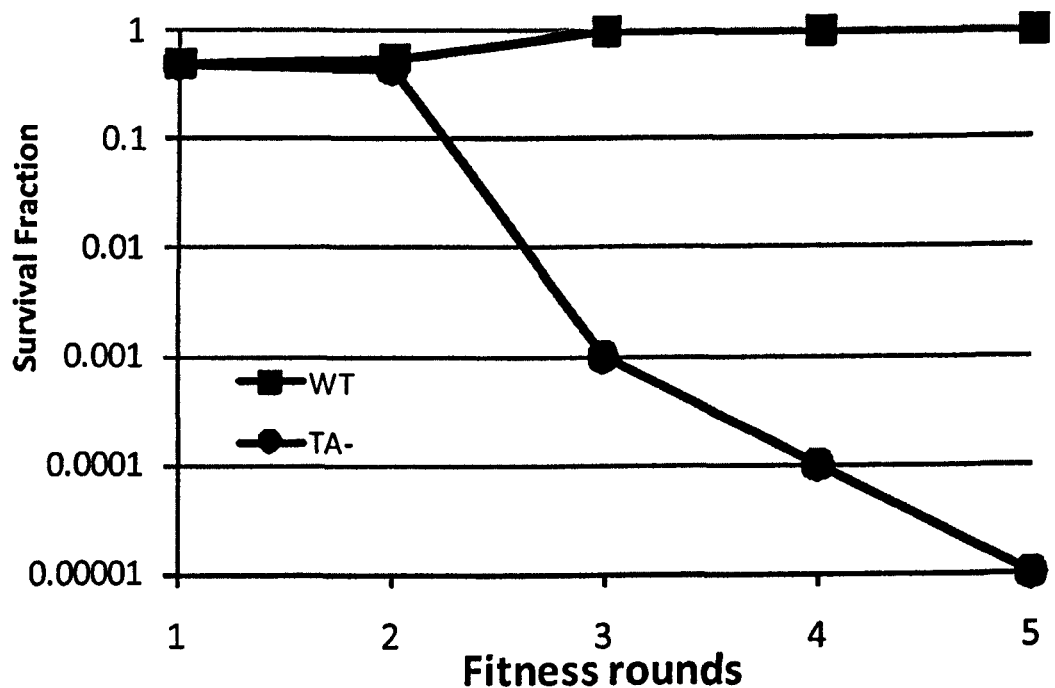
FIG. 4A is a graph demonstrating that production of antibiotic TA confers a predation fitness advantage over a TA-mutant.

It was then tested if antibiotic TA confers a selective fitness advantage over a strain that does not produce TA. In this experiment WT (DK1622) cells were mixed with the TA-mutant at a 1:1 ratio and spotted on a thick lawn of *E. coli* (MG1655) seeded on a TPM starvation agar plate (Wall et al. (1999) J. Bacteriol., 181:24-33). Under these conditions the *M. xanthus* cells can only grow by killing and consuming prey cells. After a ~10 day incubation the *M. xanthus* swarm nearly consumed the entire prey lawn. At this time the outer swarm edge was collected with a sterile wood stick. The ratio of DK1622 to TA-(ta1::kan) cells was then determined by serial dilutions and replica plating on CTT plates "with" and "without" kanamycin. Kan$^s$ colonies were scored as DK1622 and Kan$^r$ colonies were scored as TA-cells. In parallel the harvested *M. xanthus* mixture was also transferred to a fresh TPM agar plate seeded with a naive lawn of *E. coli*. This cycle was repeated a total of 4 times (~40 days). The relative ratios of DK1622 (WT) to the TA-mutant were then plotted (FIG. 4A). As illustrated, the TA-mutant was drastically less fit than the isogenic parent (WT) and was depleted from the *M. xanthus* population to undetectable levels (>5-logs). In a control experiment the TA-mutant and WT cell mixture were treated identically, except the predation experiment was done on CTT (nutrient agar, thus predation not required for growth). In this control experiment, after the 4$^{th}$ transfer there was no loss of fitness for the TA-mutant. This result demonstrates that the ta1::kan mutation is stable and that the mutant is competent at swarming and is equally fit when nutrients are available. Importantly, these experiments demonstrate that TA production confers a selective fitness advantage when microbial predation is required for growth, supporting the underlying thesis that microbial predation serves as a means to select optimized TA producing strains.

Figure 4B:
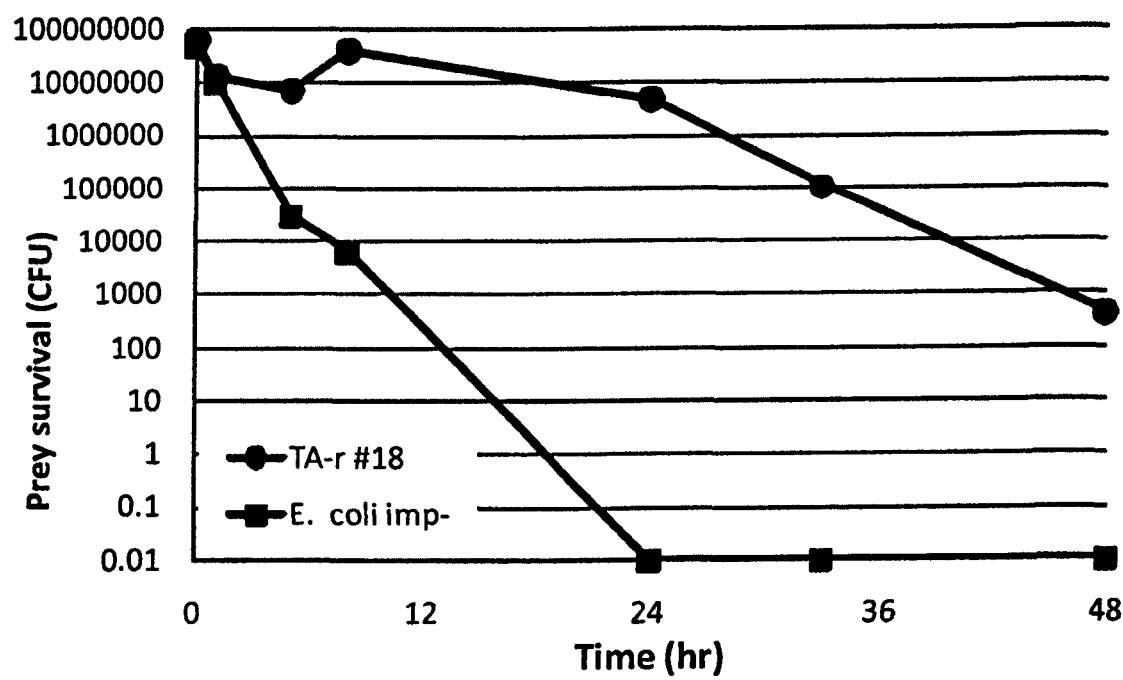
FIG. 4B is a graph demonstrating *E. coli* predation by *M. xanthus* (DK1622). Prey/predator cells were mixed at a 10:1 ratio. TA$^r$ #18 was derived from *E. coli* imp-parent by selecting TA$^r$.

Antibiotic resistance by prey cells confers a corresponding resistance to predation. In reciprocal experiments, prey mutants that are resistant to antibiotic TA were isolated to test if they become correspondingly resistant to predation by the producer strain. Here, an *E. coli* imp-permeability mutant was mutagenized and resistant colonies were selected on agar plates seeded with a TA extract. One TA$^r$ mutant (#18) was further tested. In a MIC assay mutant #18 elicited a 64-fold increase in resistance toward the TA extract as compared to the parental strain. Next, a predation assay was conducted with mutant #18 and its parental strain against DK1622. As FIG. 4B illustrates, the TA$^r$ #18 mutant exhibits a corresponding and dramatic increase in resistance toward predation. At times there is >8-log difference in killing between the TA$^r$ #18 mutant and the parent *E. coli* strain. These results again support the conclusion that antibiotic TA serves as a central weapon to kill prey bacteria.

EXAMPLE 5

Figure 4C:
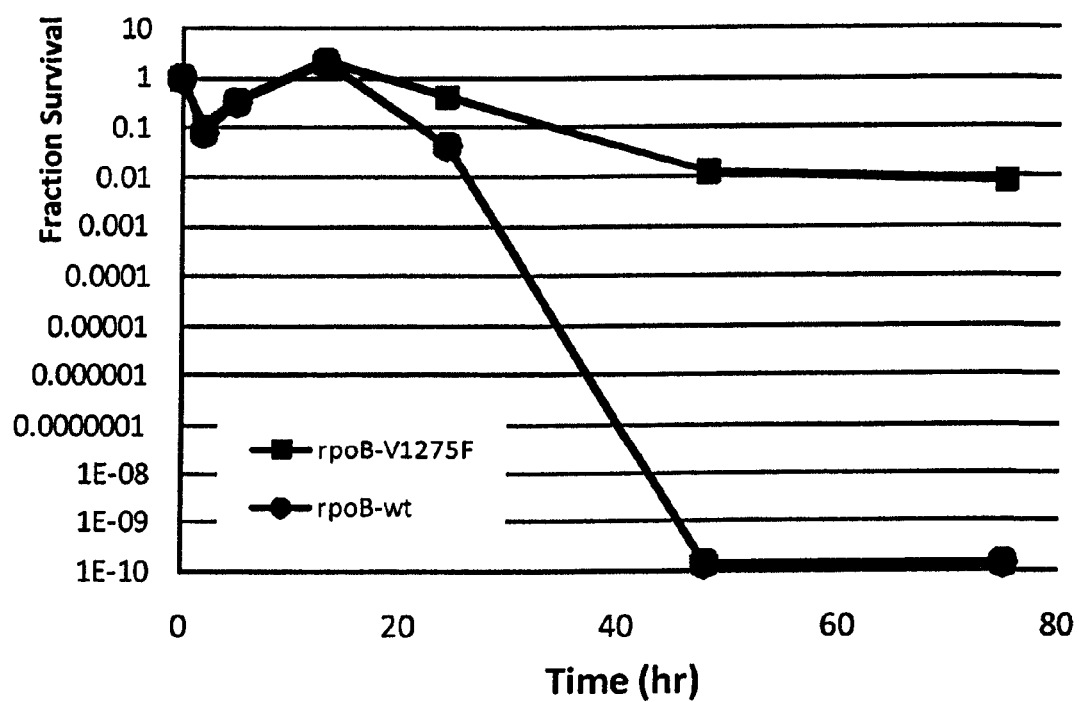
FIG. 4C provides a graph showing predation of *E. coli* by a myxobacterium, *Corrallococcus coralloides* c127, a producer of corallopyronin. PT agar was used, supplemented with 1 mM IPTG.

Notably, the molecular target for TA is not known and the molecular mechanism for TA$^r$ has not been elucidated. To unequivocally show a direct relationship between antibiotic resistance and predation resistance a better defined system was sought. One such myxobacteria system is for the NPs myxopyronin, corallopyronin and ripostatin. These three NP antibiotics have recently been shown by x-ray crystallography to bind to the "switch region" of bacterial RNA polymerase (Mukhopadhyay et al. (2008) Cell 135:295-307). In these studies the investigators also isolated RNAP mutations that conferred resistance to these antibiotics. The rpoB mutation contains a single mutation that results in a Val→Phe substitution (position 1275). Relative to wild type cells, this mutation increases antibiotic MIC values >32-fold Myx, >8-fold Cor and >16-fold Rip. It was then tested if the RpoB-V1275F mutant was also resistant to predation by the myxobacterial producer strain for corallopyronin, Corallococcus coralloides c127 (Irschik et al. (1985) J. Antibiot. (Tokyo), 38:145-152). In these experiments the rpoB allele is present on a plasmid that is under lac control; consequently predation was done in the presence of inducer (IPTG). E. coli predation was compared to an isogenic strain that has the wild type rpoB gene on a plasmid. As seen in FIG. 4C, the RpoB-V1275F mutant exhibits strong resistance towards predation. At times there was an 8-log difference in predation compared to the parental strain. Importantly, the only difference between these E. coli prey strains is a single base-pair change in rpoB. These results are consistent and support the above results with mutant #18, namely that resistance to antibiotics made by a producer strain confers a corresponding resistance to predation by that producer strain. Taken together, the data indicates that antibiotic TA plays a key role in killing prey and in predation fitness. By extension these results indicate that predation can be exploited as a means to select optimized antibiotic TA producer strains.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method for screening for a natural product producing strain of a predatory microorganism, said method comprising:
    a) obtaining a predatory microorganism;
    b) culturing the predatory microorganism of step a) under conditions wherein the only nutrient source is prey cells or under conditions wherein the predatory microorganism must compete with prey cells for growth, wherein said predatory microorganism is defective in predation of said prey cells;
    c) isolating a mutant predatory microorganism which grows under the culture conditions of step b); and
    d) screening the isolated mutant predatory microorganism of step c) to isolate a mutant predatory microorganism having altered natural product production compared to the predatory microorganism of step a),
    wherein the isolated mutant predatory microorganism having altered natural product production is said natural product producing strain.

2. The method of claim 1, further comprising the step of mutagenizing said predatory microorganism of step a).

3. The method of claim 2, wherein said predatory microorganism is mutagenized by a chemical mutagen or a physical mutagen.

4. The method of claim 1, wherein said prey cell is resistant to the natural products produced by the predatory microorganism of step a).

5. The method of claim 1, wherein said prey cell is selected from the group consisting of bacteria, fungus, parasite, mammalian cell, and cancer cell.

6. The method of claim 1, wherein said predatory microorganism is a myxobacterium.

7. The method of claim 6, wherein said myxobacterium fails to synthesize myxovirescin.

8. The method of claim 7, wherein said myxobacterium is a ta1 knockout.

9. The method of claim 1, further comprising isolating the natural product produced by the isolated mutant predatory microorganism having altered natural product production.

10. The method of claim 1, wherein said natural product is selected from the group consisting of an antimicrobial compound, an antibiotic compound, an antifungal compound, an anticancer compound, and an antiparasitic compound.

11. The method of claim 1, wherein steps b) and c) are repeated at least once.

12. The method of claim 11, wherein the isolated mutant predatory microorganism of step c) is mutagenized prior to repeating steps b) and c).

13. The method of claim 1, wherein step b) comprises culturing the predatory microorganism of step a) under conditions wherein the only nutrient source is prey cells.

14. The method of claim 1, wherein step b) comprises culturing the predatory microorganism of step a) under conditions wherein the predatory microorganism must compete with prey cells for growth.

15. The method of claim 14, wherein step b) comprises culturing said predatory microorganism and prey cells under semi-rich growth conditions.

16. The method of claim 1, wherein said predatory microorganism of step a) cannot swarm when the prey cells are the sole nutrient source.

* * * * *